US007723464B2

(12) United States Patent
Delozier et al.

(10) Patent No.: US 7,723,464 B2
(45) Date of Patent: May 25, 2010

(54) AROMATIC/ALIPHATIC DIAMINE DERIVATIVES FOR ADVANCED COMPOSITIONS AND POLYMERS

(75) Inventors: Donovan M. Delozier, Newport News, VA (US); Kent A. Watson, New Kent, VA (US); John W. Connell, Yorktown, VA (US); Joseph G. Smith, Jr., Smithfield, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 402 days.

(21) Appl. No.: 11/674,321

(22) Filed: Feb. 13, 2007

(65) Prior Publication Data

US 2008/0004419 A1 Jan. 3, 2008

Related U.S. Application Data

(60) Provisional application No. 60/774,798, filed on Feb. 13, 2006.

(51) Int. Cl.
C08G 59/10 (2006.01)
H01L 51/00 (2006.01)

(52) U.S. Cl. ............... 528/407; 528/405; 528/421; 528/418; 428/690; 313/504; 257/40; 252/301.35

(58) Field of Classification Search ............ 528/407, 528/418
See application file for complete search history.

(56) References Cited

U.S. PATENT DOCUMENTS 4,684,678 A * 8/1987 Schultz et al. ............ 523/466

| | | |
|---|---|---|
| 5,688,735 A | 11/1997 | Ewen et al. |
| 5,708,130 A | 1/1998 | Woo et al. |
| 5,710,222 A | 1/1998 | Ewen et al. |
| 5,962,631 A | 10/1999 | Woo et al. |
| 5,998,045 A | 12/1999 | Chen et al. |
| 6,204,515 B1 | 3/2001 | Bernius et al. |
| 6,355,773 B1 | 3/2002 | Weinfurtner et al. |
| 6,362,310 B1 | 3/2002 | Woo et al. |
| 6,512,083 B1 | 1/2003 | Woo et al. |
| 6,514,632 B1 | 2/2003 | Woo et al. |
| 6,593,450 B2 | 7/2003 | Woo et al. |
| 6,806,473 B2 | 10/2004 | Honda et al. |

(Continued)

FOREIGN PATENT DOCUMENTS

WO    WO 2005/113645 A1    12/2005

OTHER PUBLICATIONS

Mititelu et al, Liquid Crystalline Epoxy Thermoset Obtained from Biphenyl Mesogen, Polymer Plastics Technology and Engineering, 44, 151-162, 2005.*

(Continued)

*Primary Examiner*—Randy Gulakowski
*Assistant Examiner*—Rachel Kahn
(74) *Attorney, Agent, or Firm*—Robin W. Edwards

(57) ABSTRACT

Novel compositions of matter comprise certain derivatives of 9,9-dialkyl fluorene diamine (AFDA). The resultant compositions, whether compositions of matter or monomers that are subsequently incorporated into a polymer, are unique and useful in a variety of applications. Useful applications of AFDA-based material include heavy ion radiation shielding components and components of optical and electronic devices.

11 Claims, 1 Drawing Sheet

U.S. PATENT DOCUMENTS

| | | | |
|---|---|---|---|
| 6,808,542 | B2 | 10/2004 | Nguyen et al. |
| 6,815,505 | B2 | 11/2004 | Wu et al. |
| 6,847,162 | B2 | 1/2005 | Duggal et al. |
| 7,102,042 | B2 * | 9/2006 | Adaway et al. ............. 570/247 |
| 2005/0048314 | A1 | 3/2005 | Antonaidis et al. |

OTHER PUBLICATIONS

Belfield et al, Linear and Two-Photon Photophysical Properties of a Series of Symmetrical Diphenylaminofluorenes, Chem Mater, 2004, 16, 2267-2273.*

Kevin D. Belfield, Katherine J. Schafer, Wael Mourad, and Bruce A. Reinhardt, "Synthesis of New Two-Photon Absorbing Fluorene Derivates via Cu-Mediated Ullmann Condensations," The Journal of Organic Chemistry, Department of Chemistry, University of Central Florida and Air Force Research Laboratory (Orlando), vol. 65 ( No. 15), p. 4475-4481, (Jul. 28, 2000).

Wang et al., "Conjugated Fluorene and Silole Copolymers: synthesis, Characterization, Electronic Transition, Light Emission, Photovoltaic Cell, and Field Effect Hole Mobility." Macromoledules, 38 (6) 2005, p. 2253-2260.

Redick III et al., "Passive Protection from Hazardous Radiation during a Lunar Exploration Mission."

* cited by examiner

AROMATIC/ALIPHATIC DIAMINE DERIVATIVES FOR ADVANCED COMPOSITIONS AND POLYMERS

This application claims the benefit of U.S. patent application No. 60/774,798, filed Feb. 13, 2006, which is incorporated by reference herein in its entirety.

ORIGIN OF THE INVENTION

This invention was made in part by employees of the United States Government and may be manufactured and used by or for the Government of the United States of America for governmental purposes without the payment of any royalties thereon.

BACKGROUND OF THE INVENTION

1. Field of the Invention

The present invention relates generally to the synthesis and use of novel compositions of matter derived from 9,9-dialkyl fluorene diamine (AFDA). The resultant compositions are unique and are useful in a variety of applications, such as heavy ion radiation shielding components and as components for optical and electronic devices.

2. Description of the Related Art

Fluorene is an important component in materials applications ranging from composite building materials to organic electronics. An important feature of fluorene is that it has two locations, the bridge carbon and the aromatic rings, where various species can be attached. For example, amine groups can be placed on the aromatic rings, such as in the case of the commercially available 2,7-diaminofluorene which is commonly used in the synthesis of larger molecules and polymers.

A problem generally associated with fluorene containing molecules is their insolubility resulting from fluorene being a rigid molecule. Due to the insolubility, the addition of alkyl chains on the fluorene at the nine position (bridge carbon) is a common method for enhancing the solubility of other fluorene containing materials. For example, fluorenes containing borate ester and halogen substitution on the rings commonly contain alkyl chains at the 9 position to enhance solubility. However, the use of alkyl side chains on fluorene diamine has never been demonstrated.

Materials possessing the combined features of structural integrity and shielding against heavy ion radiation (HIR) will be required for future manned space missions. Spacecraft and space habitats are continually bombarded with small amounts of HIR, and in some instances large doses are encountered during certain events such as solar flares. HIR is dangerous to living systems and electronics and must therefore be attenuated to ensure mission safety and longevity. Hydrogen is recognized as the best element for absorbing HIR and high hydrogen content polymers, such as polyethylene, are currently used as shielding materials. However, high hydrogen content polymers are typically not good building materials and can only be used as parasitic cladding. In contrast, aromatic polymers, which contain lower amounts of hydrogen, are good structural materials and could serve as the structural components in spacecraft and space habitats. An ideal material for use in space would be a polymer composition that contains sufficient hydrogen content (aliphatic) for radiation shielding and sufficient aromatic character for structural integrity.

SUMMARY OF THE INVENTION

In accordance with the present invention, novel compositions of matter comprise central alkylated fluorene diamine derivatives having various attachments at the nitrogen atoms. The molecules and polymers generated from the AFDA derivatives are useful in numerous applications. Further, polymers including AFDA monomers alone have useful applications including radiation shielding and optical and electronic components.

In one embodiment, a derivatized 9,9-dialkyl fluorene diamine has one of the following structures:

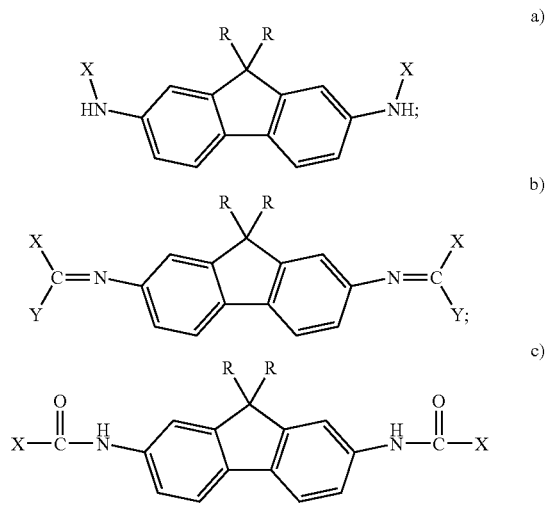

wherein X and Y are selected from the group consisting of phenyl, substituted phenyl, thiophene, substituted thiophene, pyrrole, substituted pyrrole, alkyl, alkylene, alkoxy and perfluoro, and combinations thereof;

and wherein R is an alkyl group comprising 1-30 carbon atoms.

In a further embodiment, a heavy ion radiation shield comprises an epoxy polymer, the polymer comprising the reaction product of a 9,9-dialkyl fluorene diamine monomer and a multifunctional epoxy monomer. In a still further embodiment, an electrically active composition comprises the reaction product of a derivatized 9,9-dialkyl fluorene diamine and a monomer.

DETAILED DESCRIPTION OF THE INVENTION

Figure 1:
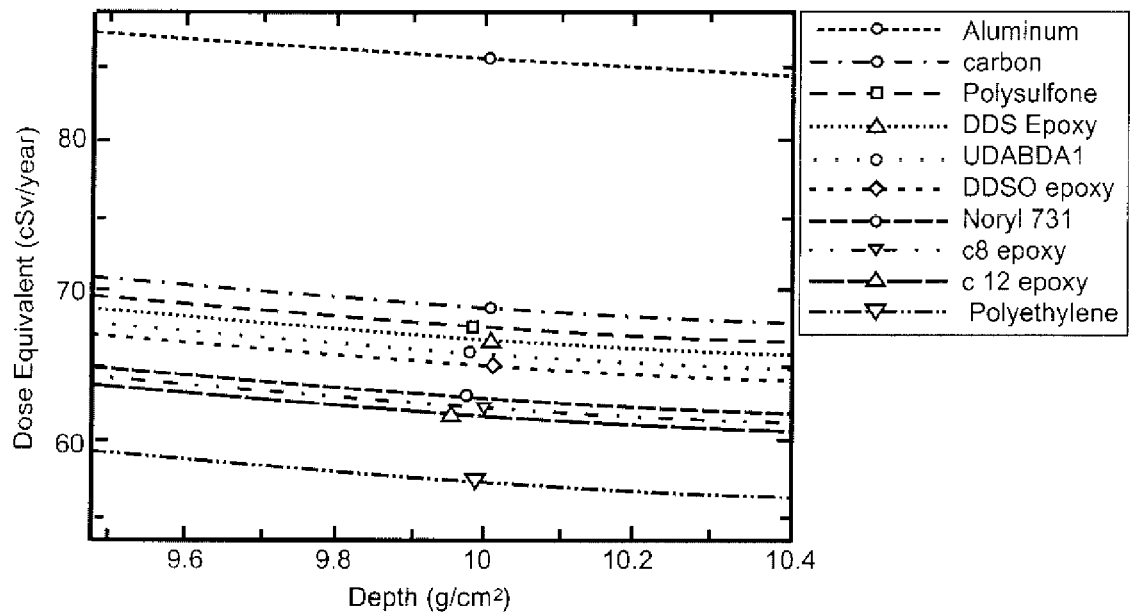
FIG. 1 illustrates analytical results for structural/radiation shielding epoxies.

The present invention is a composition of matter comprising alkyl chains on a fluorene diamine, which can further be used to produce larger molecules, including polymers that are useful as structural composite matrices, radiation shielding materials and components for optical and electronic devices.

In one embodiment, a 9,9-dialkyl fluorene diamine (AFDA) is incorporated into structural epoxy formulations.

These formulations are applicable to radiation shielding. In the epoxy formulation, a covalent bond forms between the epoxy and the diamine upon heating and curing. The aromatic amino groups of the diamine react with the epoxy to form a three-dimensional network in which the backbone is predominately aromatic in nature. This results in good mechanical properties particularly suitable for use as a composite matrix resin for structural applications. The aliphatic portion of the diamine is covalently attached to the diamine in a pendant fashion and is not involved in the crosslinking network. Aliphatic character is thereby introduced without negatively affecting the mechanical properties. In addition, the aliphatic chains cannot leach out of the system as sometimes happens when hydrogen bearing species are introduced as an additive. The combination of a structural and radiation shielding epoxy is a novel approach to providing materials that will be useful in the space environment.

In another embodiment, AFDA is used in the preparation of components for light emitting diode (LED) and photovoltaic (PV) devices. In both of these devices, three of the major components are the photon or electron acceptor, the electron (i.e., negative charged species) transport material and the hole (i.e., positive charged species) transport material. Fluorene based materials can be used in any three of these roles depending upon the electronic character of the substituents. The present invention uses AFDA containing materials as hole transport materials. The combination of phenyl rings covalently attached to nitrogen atoms is known to be a good combination to carry positive charge. In addition, the fluorene ring system is planar and planarity has been shown to be important in a molecule's ability to transport charge. Thus, large molecules and polymers prepared from fluorene diamines are perfectly suited to behave as hole transporters in LED and PV devices. However, the selection of substituents and their location necessary to achieve desired performance was not previously known.

The foregoing applications of AFDA and polymers incorporating AFDA monomers take advantage of the unique physical characteristics of the AFDA molecule. These same physical characteristics may be enhanced or improved through the creation of derivatized AFDA molecules and monomers incorporated into various polymer materials as discussed herein. The specific applications can suggest very specific functional groups that can be covalently joined to the AFDA molecule. For instance, as noted, the combination of phenyl rings covalently attached to the nitrogen atoms is noted above as being a good combination for carrying positive charge. As noted in an example that follows, additional phenyl rings and nitrogen atoms may be joined to the AFDA molecule to further enhance the electrical characteristics. Therefore, although AFDA alone is an electrically active composition, derivatized AFDA molecules and polymers formed from derivatized AFDA monomers may be created to still further improve on the already advantageous electrical properties of AFDA.

In the following example of the synthesis of an AFDA molecule, the alkyl chains are shown as having 8 carbon atoms each. Other examples may include AFDA molecules having a range of 4 to 18 carbon atoms or 1 to 30 carbon atoms. The size of the alkyl groups attached to the AFDA molecule can be varied to specifically address an intended purpose. For instance, polymers formed from an AFDA monomer having 8 carbon alkyl groups are able to serve as a superior dispersant for carbon nanotubes. The size of the alkyl group may be modified accordingly depending on a specific type of atom or material that is sought to be dispersed.

The following example details the synthesis of the AFDA molecule.

Preparation of 2,7-Dinitro-9,9-dioctylfluorene 9,9-Dioctylfluorene (30.53 g, 26.56 mmol) and glacial acetic acid (150 mL) were charged into a three-neck flask to form a biphasic mixture. The mixture was cooled to 0° C. by submersing the flask into an ice bath. Fuming nitric acid (150 mL) was added dropwise through an addition funnel over 45 min. The ice bath was slowly warmed to 55° C. over a period of 2 hrs. and then cooled to room temperature. The reaction was allowed to continue at room temperature overnight, during which time a tacky, orange precipitate formed. The contents of the reaction were slowly poured into 1200 mL ice water and stirred for 1 hr. The water was decanted from the solid and the product washed several times with water. The product was dissolved in 400 mL chloroform ($CHCl_3$) and washed sequentially with 200 mL each of water, brine, and water. The organic layer was collected and dried over magnesium sulfate and the chloroform removed by rotary evaporation to afford an orange liquid. This liquid was dissolved in 200 mL hexanes and precipitated by submersing the flask in a dry ice/acetone bath. A yellow solid was collected via filtration and washed with cold hexanes. (mp 69-73° C.). Yield=27.84 g (74.50%). $^1$H NMR (300 MHz, $CDCl_3$) δ 0.5 (m, 4H), 0.8 (t, 6H), 1.0-1.3 (m, 20H), 2.1 (m, 4H), 7.9 (s, 1H), 8.0 (s, 1H), 8.3 (d, 2H), 8.3 (d, 1H), 8.3 (d, 1H) ppm. $^{13}$C NMR (75 MHz, $CDCl_3$) δ 14, 23, 24, 29, 29, 29, 30, 32, 40, 57, 119, 122, 124, 145, 149, 154 ppm. Elemental Analysis (EA) calcd. for $C_{29}H_{42}N_2O_4$: % C, 72.47; % H, 8.39; % N, 5.83. Found: % C, 72.12; % H, 8.02; % N, 6.02.

Preparation of 2,7-Diamino-9,9-diocty-fluorene (AFDA)

2,7-Dinitro-9,9-dioctylfluorene (27.84 g, 57.93 mmol) was dissolved in absolute ethanol (90 mL) and tetrahydrofuran (THF, 50 mL). Palladium on carbon (5%, 0.5 g) was subsequently added. The mixture was placed on a Parr hydrogenator and shaken under 40 psi of hydrogen for 4 hrs. at room temperature. The mixture was filtered through CELITE® and the solvent removed by rotary evaporation to afford a red-brown liquid. The crude product was dissolved in $CHCl_3$ and stirred with decolorizing charcoal for 1 hr. at room temperature. The solution was filtered and the solvent removed by rotary evaporation to give a red liquid that slowly solidified into needle-like crystals (mp 58-63° C.). Yield=22.36 g (91.76%). $^1$H NMR (300 MHz, $CDCl_3$) δ 0.7 (m, 4H), 0.8 (t, 6H), 1.0-1.3 (m, 20H), 1.9 (m, 4H), 3.6 (s, 4H), 6.6 (m, 4H), 7.3 (d, 2H) ppm. $^{13}$C NMR (75 MHz, $CDCl_3$) δ 15, 23, 24, 30, 30, 31, 32, 41, 55, 111, 114, 119, 134, 145, 152 ppm. EA calcd. for $C_{29}H_{46}N_2$: % C, 82.80; % H, 10.54; % N, 6.66. Found: % C, 82.29; % H, 10.06; % N, 6.73.

The following sets forth the synthetic route to the formation of AFDA.

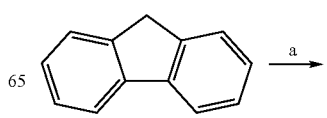

-continued

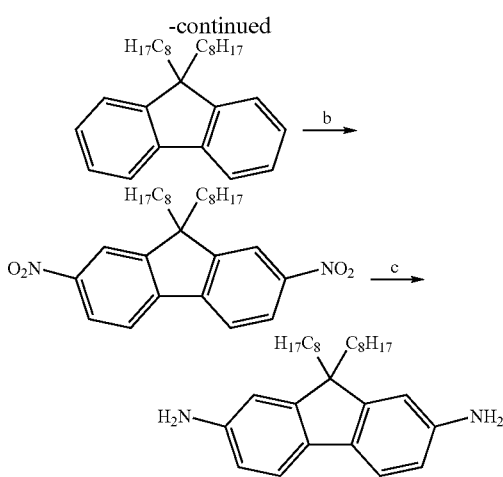

(a) THF, n-BuLi, n-octyl bromide, −78° C.

(b) acetic acid, fuming nitric acid, 55° C.

(c) 5% Pd/C, hydrogen (40 psi), THF/EtOH

The following specific examples are provided for illustrative purposes. These examples do not serve to limit the scope of the invention.

Example 1

Structural/Radiation Shielding Epoxies

AFDA was prepared by first alkylating fluorene followed by nitration. The molecule was then reduced to the diamine and used in epoxy formulation. This synthesis was illustrated above. To formulate the epoxy resin, the diamine was slowly added to tetraglycidylmethylenedianiline (TGMDA) while heating to 60° C. in a stainless steel mold. The sample was subsequently heated to 80° C. under vacuum and finally placed in a conventional oven and heated to 100° C. for 14 hrs., 120° C. for 1 hr., 140° C. for 1 hr., and 177° C. for 1 hr. The result was a 10.16 cm×10.16 cm epoxy plaque.

Computational modeling of the resin formulation was performed to determine the radiation shielding characteristics of the material. Calculations of dose, dose equivalent, and other possible metrics were made at various depths of the material using realistic galactic cosmic ray radiation environments and the NASA Langley radiation transport code HZETRN. This code is a deterministic Boltzmann equations solver that mainly transports neutrons, protons, light ions, and heavy ions. HZETRN is a well tested code that has been validated using data taken from various sources including experiments flown on International Space Station, the Shuttle, and high altitude balloons. Based on the modeling data illustrated in FIG. 1, the epoxy samples (dioctyl fluorene diamine based epoxy identified in FIG. 1 as c8 epoxy and the didodecyl fluorene diamine based epoxy identified in FIG. 1 as c12 epoxy) were closest to polyethylene in their ability to shield against HIR.

Mechanical testing was also performed on the samples to determine their potential as building materials. Compression tests were conducted using a modification of ASTM method D695. Specimens were machined into rectangular prisms of dimensions 4×4×25 mm and the crosshead speed was 1.3 mm/min. Strain was measured using a strain-gauge compressometer (knife-edge clip gauge) with a 5 mm gauge length.

Figure 2:
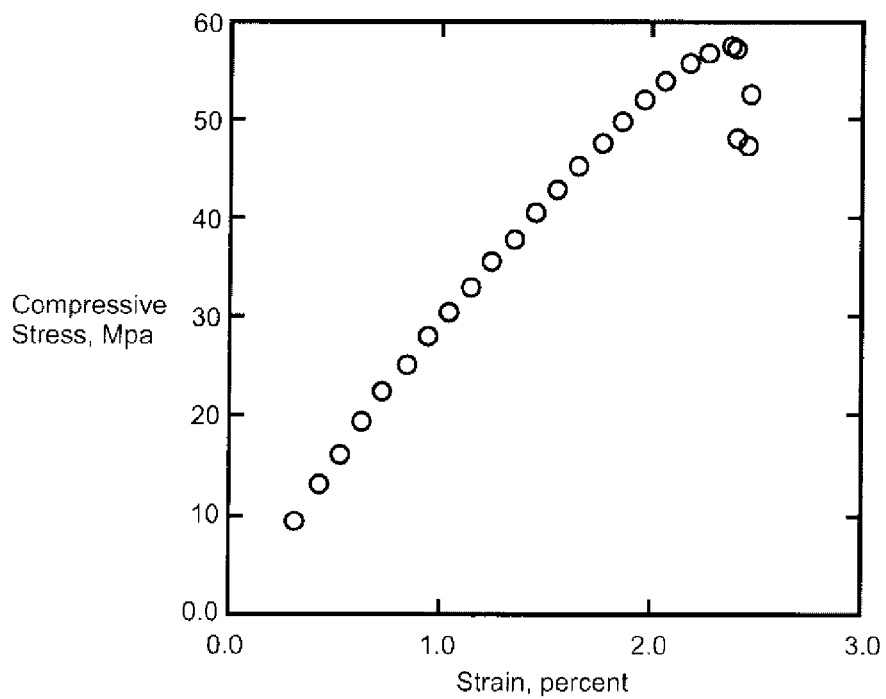
FIG. 2 illustrates stress/strain data for structural epoxy.

An example of a stress/strain curve is illustrated in FIG. 2. Compressive modulus was calculated using the initial linear portion of the curve (below 1% strain). The average modulus and apparent compressive strength from four specimens were 2.86±0.19 GPa and 52.5±3.7 MPa, respectively. (Error bounds are standard deviations)

The modulus of the neat epoxy is nearly equal to that of a typical untoughened tetrafunctional aerospace epoxy resin. The apparent strength is rather low, but should probably be regarded as a lower bound because the rather slender specimens buckled and were not in pure compression. Furthermore, while the specimens had smooth sides, their edges were chipped. These visible flaws almost certainly served to initiate the brittle failures that were observed.

As indicated earlier, the foregoing example includes tests for substituted alkyl groups of the AFDA molecule having 8 and 12 carbon atoms. It is likely that larger alkyl groups, which contain more hydrogens by definition, could likewise provide superior shielding characteristics, possibly even better than the test example described herein.

In addition to the use of the polymer including the AFDA monomer, it is possible to take advantage of the electrically active nature of the molecule in creating compositions or polymers for use in electrical devices including lighting emitting diodes and photovoltaic devices.

In addition to the AFDA molecule alone and polymers incorporating the AFDA monomer, certain derivatives of the AFDA molecule may be created for specific purposes that take advantage of the physical characteristics of the AFDA molecule. For example, the electrical capability of the AFDA molecule may be enhanced by adding additional phenyl groups and nitrogen atoms to the AFDA molecule. This AFDA derivatized molecule can exhibit superior electrical characteristics. Other examples of derivatized AFDA molecules and monomers and polymers formed therefrom are described in the following.

Specifically with respect to the polymers that incorporate AFDA derivatives, other monomers and/or ionomers can be mixed with the derivatized AFDA monomer to create a polymer having desired characteristics. For example, specific types of epoxy monomers may be combined with the derivatized AFDA molecules to obtain specific physical properties. The epoxy monomers include, but are not limited to, N,N,N',N'-Tetraglycidyl-4,4'-methylenedianiline (TGMDA), 3,4-epoxycyclohexylmethyl-3,4-epoxycyclohexane carboxylate (cycloaliphatic epoxy, Araldite CY 179) and the diglycidyl ether bisphenol A (DGEBA). Other monomers that may be strategically added to the derivatized AFDA molecule and to form polymers include difunctional monomers that possess chemical functionalities that will react with an amine that include but are not limited to halides, aldehydes, anhydrides, isocyanates, acid chlorides, carboxylic acids, sulfonyl chlorides, carbonyls, and esters, and mixtures thereof.

The following are examples of the chemical structures described herein as derivatized AFDA molecules:

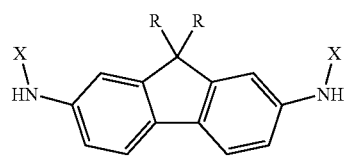

X=phenyl, substituted phenyl, thiophene, substituted thiophene, pyrrole, substituted pyrrole, alkyl, alkylene, alkoxy and perfluoro, and combinations thereof;

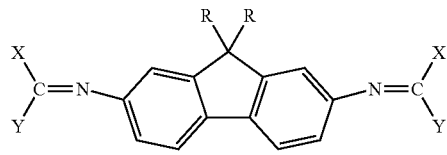

X=hydrogen, phenyl, substituted phenyl, thiophene, substituted thiophene, pyrrole, substituted pyrrole, alkyl, alkylene, alkoxy and perfluoro, and combinations thereof;

Y=hydrogen, phenyl, substituted phenyl, thiophene, substituted thiophene, pyrrole, substituted pyrrole, alkyl, alkylene, alkoxy and perfluoro, and combinations thereof;

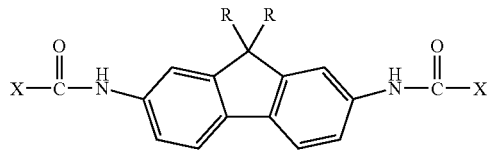

X=hydrogen, phenyl, substituted phenyl, thiophene, substituted thiophene, pyrrole, substituted pyrrole, alkyl, alkylene, alkoxy, and perfluoro, and combinations thereof;

Polymers may also be prepared by reacting certain derivatized AFDA molecules with difunctional or multifunctional monomers that possess one or more chemical functionalities selected from the group consisting of epoxides, halides, aldehydes, anhydrides, isocyanates, acid chlorides, carboxylic acids, sulfonyl chlorides, carbonyls, and esters and mixtures thereof.

The following are representative examples of the synthesis of derivatized AFDA molecules and polymers of the AFDA derivatives.

Example 2

Monomer Synthesis

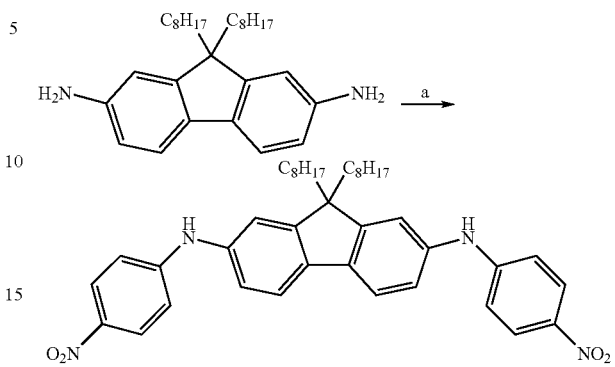

(a) Pd[P(t-Bu)$_3$]$_2$, KOH/H$_2$O, cetyltrimethyl-ammonium bromide, 1,4-bromonitrobenzene Into a 100 mL Schlenk flask was placed 103.9 mg, 0.29 mmol of cetyltrimethylammonium bromide and 293.0 mg, 0.57 mmol of Bis(tri-t-butylphosphine)palladium(0) under an Argon atmosphere. AFDA (12.00 g, 57.1 mmol) and 1,4-bromonitrobenzene (11.64 g, 57.6 mmol) were added with toluene (bubbled with nitrogen) and stirred until they completely dissolved. 10.65 g of a 45 wt % KOH solution in water (85.6 mmol) was added and the vessel was heated to 90° C. for 24 hr. Upon cooling a red precipitate formed and was collected via filtration. The powder was dried under vacuum at 100° C. The powder was dissolved in THF and poured through a celite bed. The THF was removed via rotary evaporation leaving a bright red solid. This was recrystallized from toluene yielding a bright red powder (12.158 g, 65% yield). Elemental Analysis Calc. C, 74.29%; H, 7.60%; N, 8.45%. Found C, 73.01%; H, 6.77%; N, 8.63%.

Example 3

Polymer Synthesis

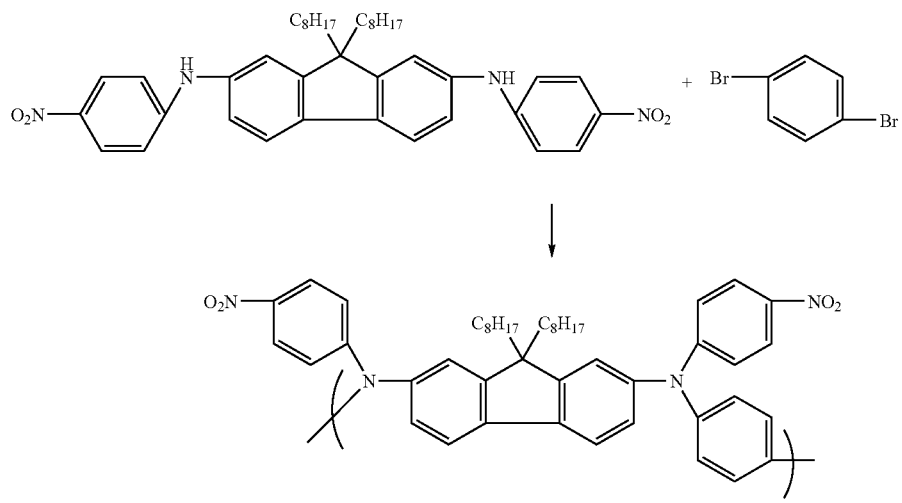

Into a 100 mL Schlenk flask was placed cetyltrimethylammonium bromide (8.3 mg) and Bis(tri-t-butylphosphine)palladium(0) (23.4 mg, mmol) under an Argon atmosphere. The dinitro compound (1.5137 g, 2.28 mmol) and 1,4-dibromobenzene (0.5387 g, 2.28 mmol) were added with toluene (bubbled with nitrogen) (15 mL) and stirred until they completely dissolved. A 45 wt % KOH solution in water (0.8528 g) was added and the vessel was heated to 90° C. for 48 hr. The contents of the vessel were poured through a Buchner funnel and the toluene was removed via rotary evaporation. The remaining reddish oil was dissolved in CHCl$_3$ washed with water and poured through celite. The CHCl$_3$ was removed via rotary evaporation yielding a red solid. 3.192 g of the powder was placed in a Soxhlet extractor and was extracted for 20 hrs. with acetone. The polymer was dissolved in CHCl$_3$ and then precipitated in hexanes. The powder was dried under vacuum (1.567 g).

compound (1.5137 g, 2.28 mmol) and the dibromo compound (1.2524 g, 2.28 mmol) were added with toluene (bubbled with nitrogen) (15 mL) and stirred until they completely dissolved. A 45 wt % KOH solution in water (0.8528 g) was added and the vessel was heated to 90° C. for 48 hr. The contents of the vessel were poured through a Buchner funnel and the toluene was removed via rotary evaporation. The remaining reddish oil was dissolved in CHCl$_3$ washed with water and poured through Celite®. The CHCl$_3$ was removed via rotary evaporation yielding a red tacky solid.

Example 4

Polymer Synthesis

Example 5

Polymer Synthesis

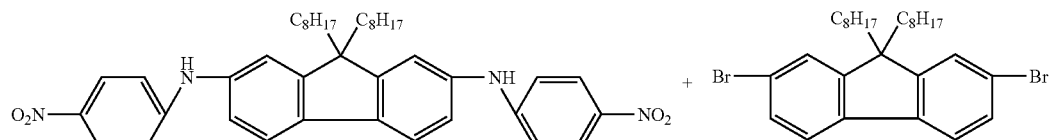

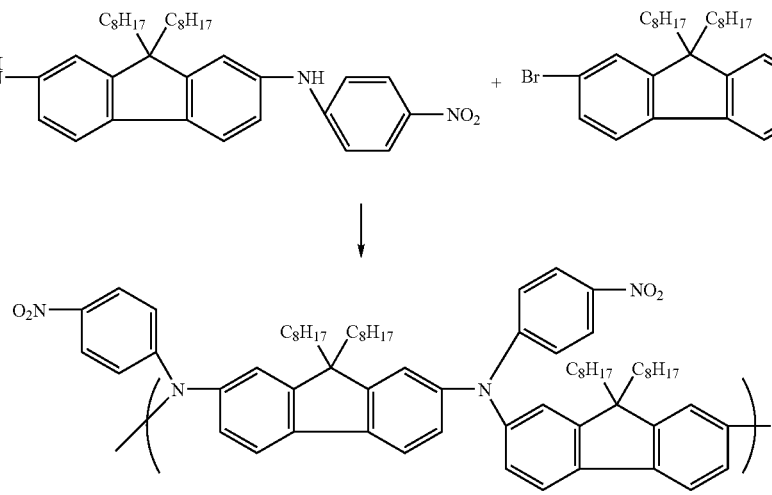

Into a 100 mL Schlenk flask was placed cetyltrimethylammonium bromide (8.3 mg) and Bis(tri-t-butylphosphine)palladium(0) (23.4 mg) under an Argon atmosphere. The dinitro

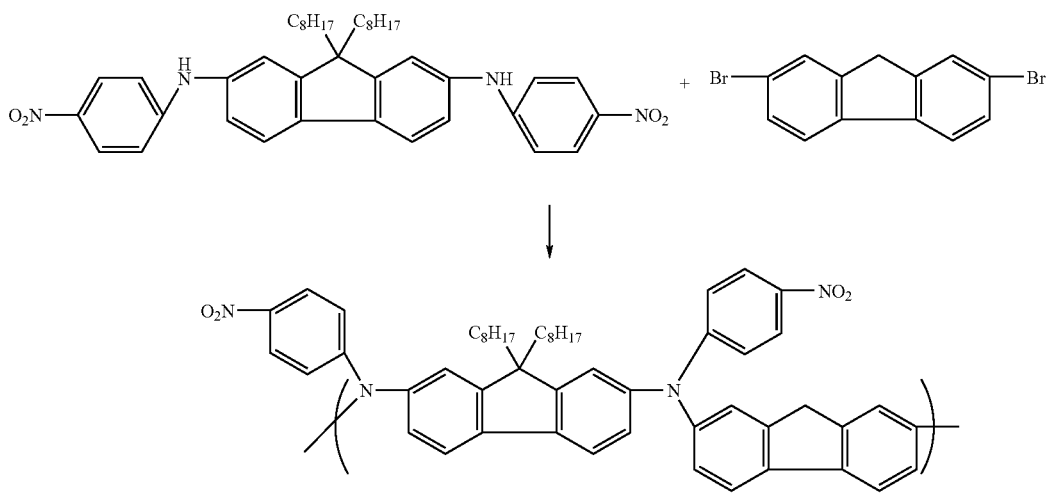

Into a 100 mL Schlenk flask was placed cetyltrimethylammonium bromide (8.3 mg) and Bis(tri-t-butylphosphine)palladium(0) (23.4 mg) under an Argon atmosphere. The dinitro compound (1.5137 g, 2.28 mmol) and the dibromo compound (0.7400 g, 2.28 mmol) were added with toluene (bubbled with nitrogen) (15 mL) and stirred until they completely dissolved. A 45 wt % KOH solution in water (0.8528 g) was added and the vessel was heated to 90° C. for 24 hr. The solid polymer had precipitated and was isolated by filtration and dried.

While the invention has been described with reference to specific embodiments thereof, it will be understood that numerous variations, modifications and additional embodiments are possible, and all such variations, modifications, and embodiments are to be regarded as being within the spirit and scope of the invention.

We claim:

1. A polymer comprising the product of the reaction of a derivatized 9,9-dialkyl fluorene diamine and a monomer comprising one or more chemical epoxide functionalities, wherein the derivatized 9,9-dialkyl fluorene diamine is:

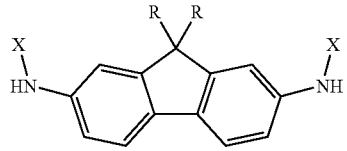

wherein X is selected from the group consisting of phenyl, substituted phenyl, thiophene, substituted thiophene, pyrrole, substituted pyrrole, alkyl, alkylene, alkoxy and perfluoro, and combinations thereof; and wherein R is an alkyl group comprising 1-30 carbon atoms.

2. A polymer as in claim 1, wherein R is an alkyl group comprising 4-18 carbon atoms.

3. A polymer as in claim 2, wherein R is an alkyl group comprising 8 carbon atoms.

4. A heavy ion radiation shield comprising a polymer as in claim 1.

5. A heavy ion radiation shield as in claim 4, wherein R comprises 4-18 carbon atoms.

6. A heavy ion radiation shield as in claim 5, wherein R comprises 8 carbon atoms.

7. The polymer of claim 1, wherein the polymer is electrically active.

8. A component of a light emitting diode comprising the electrically active polymer as in claim 7.

9. A component of a photovoltaic device comprising the electrically active polymer as in claim 7.

10. A heavy ion radiation shield comprising a polymer, wherein the polymer comprises the product of the reaction of a derivatized 9,9-dialkyl fluorene diamine and a monomer, wherein the derivatized 9,9-dialkyl fluorene diamine is:

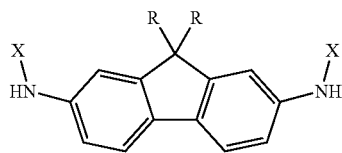

and the monomer comprises one or more chemical epoxide functionalities, and wherein the polymer further comprises the product of the reaction with an epoxy selected from the group consisting of N,N,N',N'-tetraglycidyl-4,4'-methylenedianiline (TGMDA), 3,4-epoxycyclohexylmethyl-3,4-epoxycyclohexane carboxylate (cycloaliphatic epoxy, Araldite CY 179) and diglycidyl ether bisphenol A (DGEBA) wherein X is selected from the group consisting of phenyl, substituted phenyl, thiophene, substituted thiophene, pyrrole, substituted pyrrole, alkyl, alkylene, alkoxy and perfluoro, and combinations thereof; and wherein R is an alkyl group comprising 1-30 carbon atoms.

11. A heavy ion radiation shield as in claim 10, wherein the epoxy comprises N,N,N',N'-tetraglycidyl-4,4'-methylenedianiline.

* * * * *